United States Patent
Landis

(10) Patent No.: US 9,841,302 B2
(45) Date of Patent: Dec. 12, 2017

(54) WIRE SEAL FOR DETECTOR ASSEMBLY

(71) Applicant: Scott Technologies, Inc., Boca Raton, FL (US)

(72) Inventor: Jeffrey Lynn Landis, Waxhaw, NC (US)

(73) Assignee: Scott Technologies, Inc., Boca Raton, FL (US)

( * ) Notice: Subject to any disclaimer, the term of this patent is extended or adjusted under 35 U.S.C. 154(b) by 166 days.

(21) Appl. No.: 14/843,290

(22) Filed: Sep. 2, 2015

(65) Prior Publication Data
US 2015/0377659 A1 Dec. 31, 2015

Related U.S. Application Data

(63) Continuation of application No. PCT/US2014/019444, filed on Feb. 28, 2014.
(Continued)

(51) Int. Cl.
*G01D 11/24* (2006.01)
*G01N 33/00* (2006.01)

(52) U.S. Cl.
CPC ....... *G01D 11/245* (2013.01); *G01N 33/0057* (2013.01)

(58) Field of Classification Search
CPC  G01D 11/245; G01F 23/268; G01N 33/0009; G01N 27/4062; G01N 27/407; G01N 27/4078
See application file for complete search history.

(56) References Cited

U.S. PATENT DOCUMENTS 3,472,701 A  10/1969  Selover, Jr. et al.
4,376,227 A * 3/1983  Hilborn .................... G01K 1/14
                                                            136/230
(Continued)

FOREIGN PATENT DOCUMENTS

CN       1603810 A    4/2005
CN     101206190 A    6/2008
(Continued)

OTHER PUBLICATIONS

XP055227782, "Temposonics Tempoguard (TM) Explosion-proof housing", Jan. 1, 2013. Retrieved from www.mtssensors.com on Nov. 11, 2015.
(Continued)

*Primary Examiner* — David A Rogers
(74) *Attorney, Agent, or Firm* — Christopher & Weisberg, P.A.

(57) ABSTRACT

A detector head assembly of a sensor includes a detector body having an internal channel extending a longitudinal length. The detector body is configured to hold a sensor cartridge that includes a sensing element. The detector head assembly includes a wire having a conductor. The wire extends into the internal channel of the detector body such that an end of the conductor is configured to be operatively connected to the sensing element. The detector head assembly includes a wire seal having a generally pliable sealant held within the internal channel of the detector body. The generally pliable sealant is configured to be longitudinally compressed along the longitudinal length of the internal channel during assembly of the detector head assembly such that the generally pliable sealant moves into and fills one or more voids between the wire and the detector body for sealing the wire to the detector body.

17 Claims, 6 Drawing Sheets

Related U.S. Application Data

(60) Provisional application No. 61/772,223, filed on Mar. 4, 2013.

(56) References Cited

U.S. PATENT DOCUMENTS

| | | | | |
|---|---|---|---|---|
| 4,484,022 | A * | 11/1984 | Eilentropp | H01R 4/70 156/49 |
| 4,902,962 | A * | 2/1990 | Ishikawa | G01F 23/268 324/441 |
| 5,616,825 | A * | 4/1997 | Achey | G01N 27/4062 204/424 |
| 5,625,167 | A * | 4/1997 | Van Noten | H02G 15/043 174/138 F |
| 5,630,729 | A * | 5/1997 | Francis | H01R 33/09 439/548 |
| 5,795,454 | A | 8/1998 | Friese et al. | |
| 5,846,391 | A | 12/1998 | Friese et al. | |
| 6,148,681 | A * | 11/2000 | Gravel | G01F 23/268 73/866.5 |
| 6,273,432 | B1 | 8/2001 | Weyl et al. | |
| 6,287,280 | B1 * | 9/2001 | Lampropoulos | A61M 39/0693 604/165.01 |
| 6,408,680 | B2 | 6/2002 | Friese et al. | |
| 6,419,236 | B1 * | 7/2002 | Janian | F16J 15/3212 277/553 |
| 7,135,870 | B2 * | 11/2006 | Mohajer | G01N 22/00 324/639 |
| 7,288,719 | B2 | 10/2007 | Barnhard et al. | |
| 7,401,511 | B2 * | 7/2008 | Dietmeier | G01F 23/00 73/290 R |
| 7,622,677 | B2 | 11/2009 | Barberree et al. | |
| 7,894,206 | B2 * | 2/2011 | Kopp | G01D 11/30 361/752 |
| 8,381,576 | B2 | 2/2013 | Schlichte et al. | |
| 8,951,229 | B2 * | 2/2015 | Bonnette | A61M 39/0613 604/164.01 |
| 9,291,635 | B2 * | 3/2016 | Bailey | G01N 30/16 |
| 2005/0109077 | A1 | 5/2005 | Weyl et al. | |
| 2007/0180717 | A1 * | 8/2007 | Kopp | G01D 11/30 33/366.11 |
| 2008/0073104 | A1 | 3/2008 | Barberree et al. | |
| 2008/0149483 | A1 | 6/2008 | Robison | |
| 2009/0084160 | A1 * | 4/2009 | Bristol | G01D 11/245 73/31.05 |
| 2009/0211808 | A1 * | 8/2009 | Falk | H01R 13/5216 174/667 |
| 2009/0315278 | A1 | 12/2009 | Dirienzo, Jr. et al. | |
| 2010/0220491 | A1 * | 9/2010 | Johnson | B60Q 1/0088 362/520 |
| 2011/0259084 | A1 | 10/2011 | Atsumi et al. | |
| 2012/0153535 | A1 | 6/2012 | Robison | |
| 2012/0192623 | A1 * | 8/2012 | Adami | G01N 33/007 73/31.05 |
| 2013/0098140 | A1 * | 4/2013 | Bailey | G01N 30/16 73/23.35 |

FOREIGN PATENT DOCUMENTS

| | | |
|---|---|---|
| CN | 101285694 A | 10/2008 |
| CN | 201737973 U | 2/2011 |
| CN | 202002660 U | 10/2011 |
| JP | 2001-188060 A | 7/2001 |

OTHER PUBLICATIONS

XP055227786, "Explosion Protection Gas Detection Systems", Jan. 1, 2009. Retrieved from www.draeger.com on Nov. 11, 2015.

State Intellectual Property Office of the People's Republic of China, Notification of the First Office Action (PCT Application in the National Phase), dated Nov. 1, 2016, consisting of 20-pages.

International Search Report and Written Opinion, dated Jun. 20 2014, for International Application Serial No. PCT/US2014/019444, International Filing Date Feb. 28, 2014, consisting of 12-pages.

Chinese Office Action and English translation of same dated Aug. 21, 2017 issued in corresponding Chinese Patent Application No. 201480011651.9, consisting of 20-pages.

* cited by examiner

WIRE SEAL FOR DETECTOR ASSEMBLY

CROSS-REFERENCE TO RELATED APPLICATIONS

This application is a continuation of International Application No. PCT/US2014/019444 filed Feb. 28, 2014, which claims priority to and the benefit of the filing date of U.S. Provisional Application No. 61/772,223, filed Mar. 4, 2013, both of which are hereby incorporated by reference in their entirety.

BACKGROUND

The subject matter disclosed herein relates generally to detector assemblies used in environments containing explosive and/or combustible gases and/or vapors.

Environmental detection systems may include a variety of sensors for detecting the presence and/or concentration of various chemicals in various environments. For example, sensors may be used in hazardous environments for detecting the presence and/or concentration of hazardous (e.g., volatile, combustible, explosive, and/or toxic) gases and/or vapors.

At least some known detection systems are used in environments containing combustible and/or explosive gases and/or vapors. The sensors of such detection systems are typically mounted to a mounting structure having an explosion-resistant housing. The explosion-resistant housing has an interior chamber that is hermetically sealed to separate a volume of space within the housing from the environment. The sensors include one or more wires that connect a sensing element of the sensor to one or more processing components, power supply components, and/or communication components, each of which may be held within the interior chamber of the housing or further upstream. The wire(s) extend from the sensing element and pass through a body of the sensor into the interior chamber of the housing. The interior chamber of the housing is separated from the environment such that any combustion and/or explosion within the interior chamber is less likely to extend into the environment.

At least some known detection systems use heat-cured epoxy sealants to seal the wire(s) to the body of the sensor in an attempt to prevent any combustion and/or explosion within the interior chamber from extending into the environment through the interface between the wire(s) and the body of sensor (i.e., along the path of the wire(s) through the body of the sensor). But, such heat-cured epoxy sealants may lose adhesion to the body of the sensor over time, for example because of fatigue, environmental and/or chemical exposure, and/or different thermal expansion and contraction of the different materials of the epoxy and the body of the sensor. Moreover, heat-cured epoxy sealants may have tolerance issues with regard to the density and/or thermal coefficient of expansion of the epoxy, for example because of processing variations in material compounding, mixing, and/or post curing temperatures. The loss of adhesion and/or the tolerance issues of the heat-cured epoxy may cause the heat-cured epoxy to fail to maintain a seal at the interface between the wire(s) and the body of the sensor, which may enable an explosion and/or combustion within the interior chamber of the housing to extend into the environment. Accordingly, using a heat-cured epoxy sealant to seal the wire(s) to the body of the sensor may present safety issues in explosive and/or combustible environments.

BRIEF DESCRIPTION

In an embodiment, a detector head assembly of a sensor includes a detector body having an internal channel extending a longitudinal length. The detector body is configured to hold a sensor cartridge that includes a sensing element. The detector head assembly includes a wire having a conductor. The wire extends into the internal channel of the detector body such that an end of the conductor is configured to be operatively connected to the sensing element. The detector head assembly includes a wire seal having a generally pliable sealant held within the internal channel of the detector body. The generally pliable sealant is configured to be longitudinally compressed along the longitudinal length of the internal channel during assembly of the detector head assembly such that the generally pliable sealant moves into and fills one or more voids between the wire and the detector body for sealing the wire to the detector body.

In an embodiment, a detector head assembly of a sensor includes a detector body having an internal channel extending a longitudinal length. The detector body is configured to hold a sensor cartridge that includes a sensing element. The detector head assembly includes a wire having a conductor. The wire extends into the internal channel of the detector body such that an end of the conductor is configured to be operatively connected to the sensing element. The detector head assembly includes a wire seal having a generally pliable sealant held within the internal channel of the detector body. The generally pliable sealant is configured to flow under dynamic pressure when exposed to at least one of an explosive gas pressure or an explosive vapor pressure such that a seal pressure between the wire and the detector body is increased.

In an embodiment, a detector assembly includes a mounting structure having an interior chamber, and a sensor configured to be mounted to the mounting structure. The sensor includes a detector body having an internal channel extending a longitudinal length. The detector body is configured to hold a sensor cartridge that includes a sensing element. The detector body is configured to be mounted to the mounting structure such that the internal channel communicates with the interior chamber of the mounting structure. The sensor includes a wire having a conductor. The wire extends from the interior chamber of the mounting structure and into the internal channel of the detector body such that an end of the conductor is configured to be operatively connected to the sensing element. The sensor includes a wire seal having a generally pliable sealant held within the internal channel of the detector body. The generally pliable sealant is configured to be longitudinally compressed along the longitudinal length of the internal channel during assembly of the detector head assembly such that the generally pliable sealant moves into and fills one or more voids between the wire and the detector body for sealing the wire to the detector body.

DETAILED DESCRIPTION

The invention includes a gas detection head with sealed wire leads for use in potentially hazardous areas where explosive gas or vapors may be present in the atmosphere, and method thereof, used to seal the wiring in the detector head assembly within an explosion proof housing. As such, when the detector head is mounted in an explosion proof enclosure the wire seal will not allow explosive gas or vapor to penetrate the wire seal. An explosion proof gas detector head with dynamic flame path wire seal has a sensor connector assembly with a plurality of sensor connection wires. The wires have single round solid conductors. A thickness of pliable sealant between rigid sealants is compressed with a follower sleeve having an anti-rotation pin and retained into an explosion proof detector head housing using a compression nut.

The invention provides a sealing of the wiring from the sensor connector as it passes through the detector head housing to the electronics inside an explosion proof enclosure. The invention eliminates the use of heat cured epoxy sealants which are susceptible to loss of adhesion to housing materials due to time, environmental exposure, chemical exposure, and thermal expansion and contraction of dissimilar materials, as well as issues of tolerances in density and thermal coefficient of expansion in cured sealants. The invention preferably utilizes high temperature rigid and pliable sealant materials.

Figure 1:
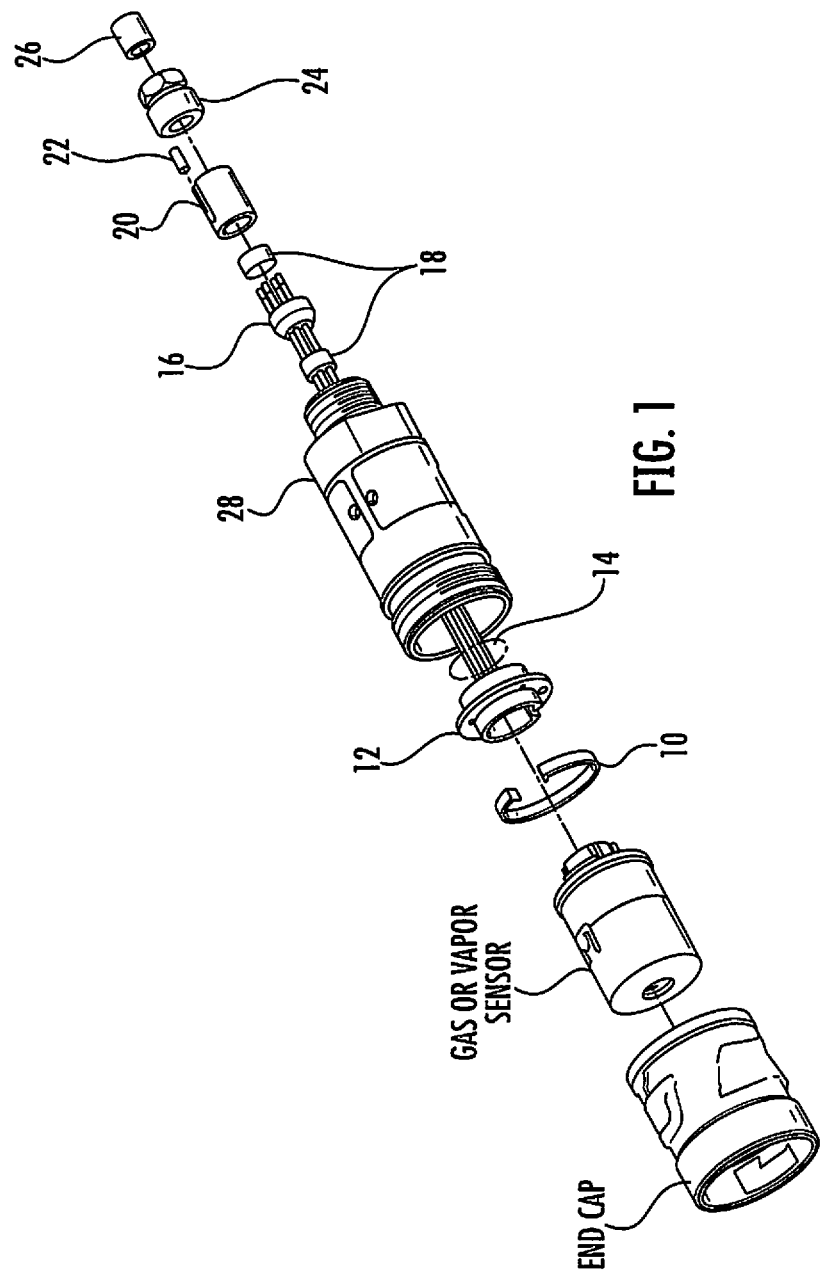
FIG. 1 illustrates an expanded view of the detector head assembly with gas or vapor sensor and end cap.
Figure 2:
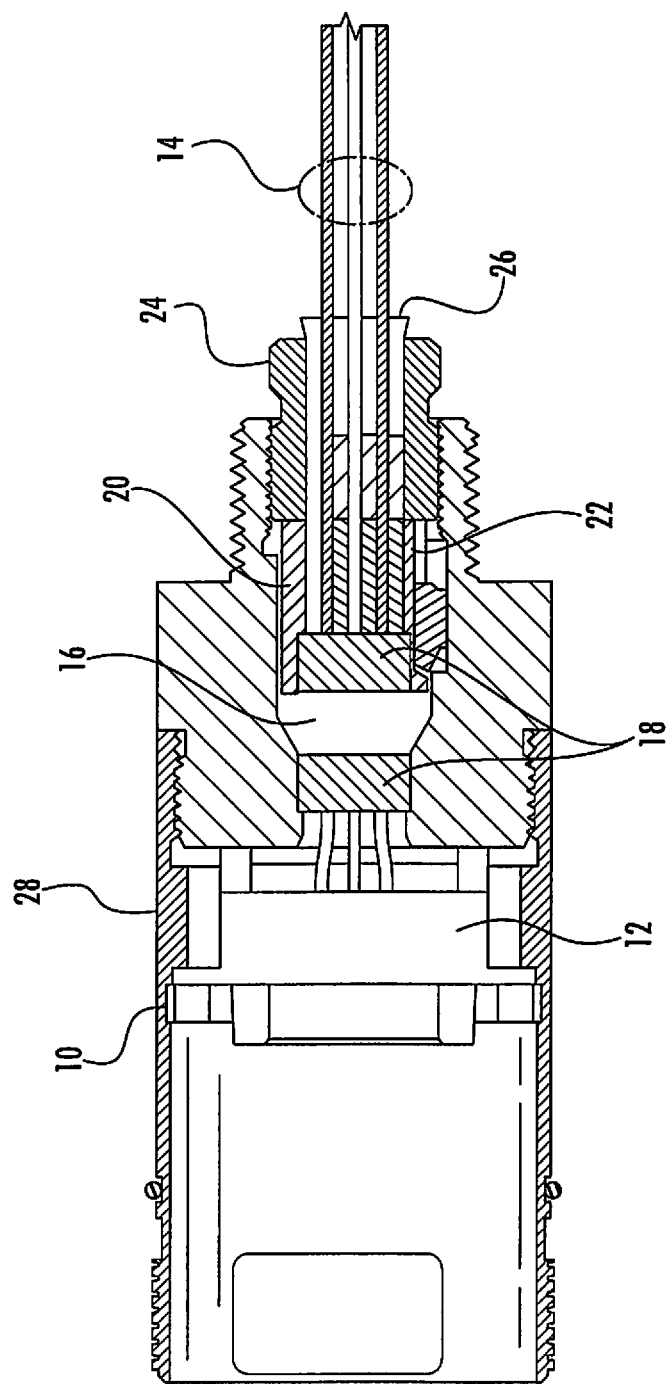
FIG. 2 illustrates a section view showing the detector head wire seal components assembled within an explosion proof housing.

As seen in FIGS. 1 and 2, the invention includes a sensor connector assembly 12 with a plurality of sensor connection wires 14 having single round solid conductors and a thickness of polymer insulation. The sensor connector assembly 12 is retained in the detector head housing 28 with retaining ring 10. The connection wires 14 are sealed to the detector head housing 28 by sliding the wires through the preformed holes in the pliable 16 and rigid 18 sealants until seated in the detector head housing 28. The seal around the wires is achieved by compressing the pliable sealant 16 between the rigid sealants 18. Preferably pliable sealant 16 includes semi-rigid or expanded polymers such as polytetrafluoroethylene (Teflon), elastomers such as but not limited to natural rubber, graphite, isoprene, styrene-butadiene, butyl, ethylene propylene, nitrile, neoprene, chlorosulphonated polyethylene, silicone, fluorosilicone, and other like compositions. Most preferably the pliable sealant is a preformed graphite Grade GHA-J with a corrosion resistant inhibitor. Preferred rigid sealants include, for example without limitation, polymers polytetrafluoroethylene (Teflon), polyphenylene sulfide, polysulfone, polyethersulfone, polyetheretherketone, polyetherimide, polyphenylene oxide, ceramic, metals with and without protective coatings, and other like compositions. Preferably the rigid sealant is ceramic $Al_2O_3$, at least 96% pure. Still more preferably the invention includes a graphite pliable sealant 16 and rigid ceramic sealant 18. Most preferably the invention includes a preformed graphite Grade GHA-J with a corrosion resistant inhibitor pliable sealant 16 and ceramic $Al_2O_3$, at least 96% pure rigid sealant 18. The sealants 16, 18 are compressed in the housing 28 by means of the follower sleeve 20. The follower sleeve 20 is pushed by the compression nut 24 as it is threaded into the detector head housing 28. This is controlled by applying rotational torque to compression nut 24, until the pliable sealant 16, flows around the wiring 14 and the rigid sealants 18, filling the voids between the wires and the sealant cavity in detector head housing 28. The pliable sealant 10 flows under dynamic pressure providing an increase in seal pressure when subjected to explosive gas or vapor pressure.

Pliable sealant 16 flows under dynamic pressure providing an increase in seal pressure when subjected to explosive fault conditions. This controlled dynamic compression seal design allows the detector head assembly to be utilized at operating temperatures from −40° C. to +85° C. in explosion proof enclosures with explosion pressures up to 6000 psi (413.685 Bar).

The follower sleeve 20 is held from rotation by the anti-rotation pin 22. To prevent damage to the polymer insulation on connection wiring 14 as is egresses from the assembly, a rubber sleeve 26 is assembled over the connection wiring 14, and pressed into and retained in the hole in compression nut 24.

Preferably the invention includes a gas detector head with dynamic flame path wire seal, as shown in FIGS. 1 and 2, having a gas sensor connector assembly 12. The gas detector head with dynamic flame path wire seal has a sensor connector assembly with a plurality of sensor connection wires with single round solid conductors with a thickness of polymer insulation 14, more preferably with preformed pliable sealant 16, still more preferably with preformed pliable sealant between rigid sealants 18, and most preferably compressed with a follower sleeve 20. The follower sleeve 20 preferably has an anti-rotation pin 22, which is more preferably is retained into detector head housing 28, which is most preferably retained with compression nut 24.

While certain embodiments of the disclosure have been described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

Figure 3:
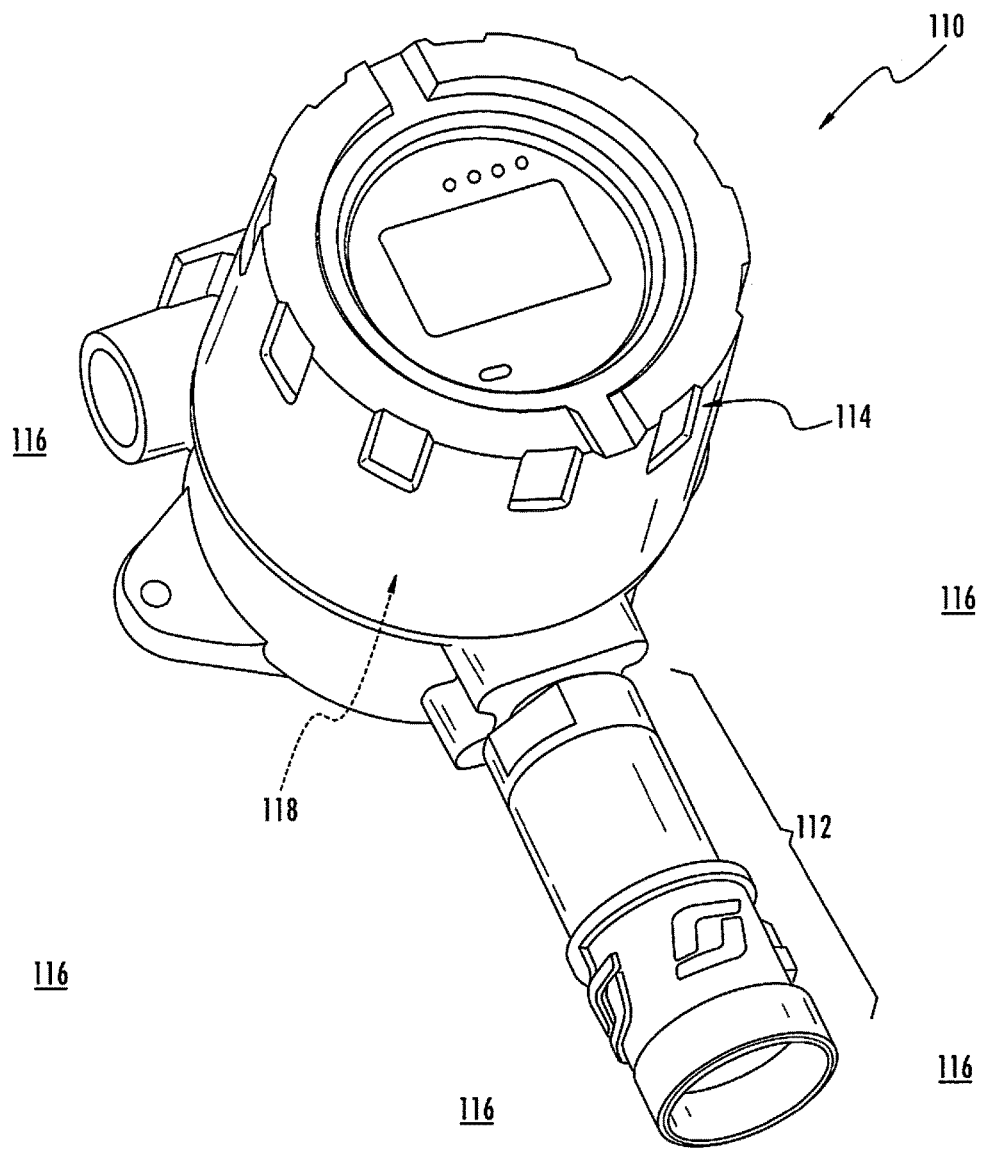
FIG. 3 is a perspective view of an embodiment of a detector assembly.

FIG. 3 is a perspective view of an embodiment of a detector assembly 110. The detector assembly 110 includes a sensor 112 and a mounting structure 114. As shown in FIG. 3, the sensor 112 is mounted to the mounting structure 114 such that the sensor 112 is exposed within an environment 116 for sensing one or more parameters within the environment 116. The sensor 112 may be any type of sensor that is configured to sense any parameter(s). For example, in some embodiments, the sensor 112 is configured to detect the presence and/or amount of any substance (e.g., a vapor and/or a gas, such as, but not limited to, a volatile gas, a volatile vapor, a combustible gas, a combustible vapor, an explosive gas, an explosive vapor, a toxic gas, a toxic vapor, and/or the like) within the environment 116. Examples of other parameters that may be sensed by the sensor 112 include, but are not limited to, pressure, density, temperature, relative humidity, and/or the like. The sensor 112 may be used in any application and the environment 116 may be any environment, such as, but not limited to, a sump area, a holding area, a well, and/or the like. In some embodiments, the environment 116 is a hazardous environment, such as, but not limited to, petroleum well, a power plant, a petroleum pipe system, and/or the like. For example, the sensor 112 may be used within a hazardous environment for detecting the presence and/or amount of a volatile, combustible, explosive, and/or toxic gas within the hazardous environment.

The mounting structure 114 supports the sensor 112 such that the sensor 112 is exposed within the environment 116 for performing sensing operations. The mounting structure 114 may include processing components, power supply components, communications components, and/or the like that support operation of the sensor 112. For example, an interior chamber 118 of the mounting structure 14 may hold one or more electrical power sources (not shown; e.g., a battery and/or the like) and/or one or more electrical power distribution components (not shown; e.g. electrical wires and/or cables, circuit boards, switches, relays, transformers, capacitors, voltage regulators, current regulators, and/or the like) for supplying electrical power to the sensor 112 to power operation of the sensor 112. The interior chamber 118 of the mounting structure 14 may hold one or more processing components (not shown; e.g., computers, processors, controllers, microprocessors, circuit boards, microcontrollers, memories, integrated circuits, and/or the like) that process signals from the sensor 112 that represent the parameter(s) sensed by the sensor 112. Processing of signals from the sensor 112 optionally includes data logging operations. In addition or alternative to the power supply component(s) and/or the processing component(s), the interior chamber 118 of the mounting structure 114 may hold one or more communication components (not shown; e.g., electrical wires and/or cables, circuit boards, other electrical pathways, switches, relays, communication nodes, and/or the like) that enables the sensor 112 to communicate with a remote location and/or other sensors. The remote location and/or the other sensors may contain one or more processing components and/or electrical power components that relate to operation of the sensor 112.

The mounting structure 114 may include any structure, means, configuration, and/or the like that enables the mounting structure 114 to support the sensor 112 within the environment 116. In the illustrated embodiment, the interior chamber 118 of the mounting structure 114 is hermetically sealed to separate a volume of space within the mounting structure 114 from the environment 116. Specifically, in the illustrated embodiment, the mounting structure 114 is an explosion-resistant housing and interior chamber 18 holds one or more processing components, power supply components, and/or communication components that relate to operation of the sensor 112. The interior chamber 118 is separated from the environment 116 such that any combustion and/or explosion within the interior chamber 118 is less likely to extend into the environment 116. As such, any combustion and/or explosion that occurs within the interior chamber 118 is less likely to cause any substance within the environment to combust and/or explode. The illustrated embodiment of the mounting structure 114 may be commonly referred to as an "explosion-proof transmitter enclosure." Although described above as being an active sensor that requires a supply of electrical power to operate, the sensor 112 may be a passive sensor that does not require a supply of electrical power to operate.

Figure 4:
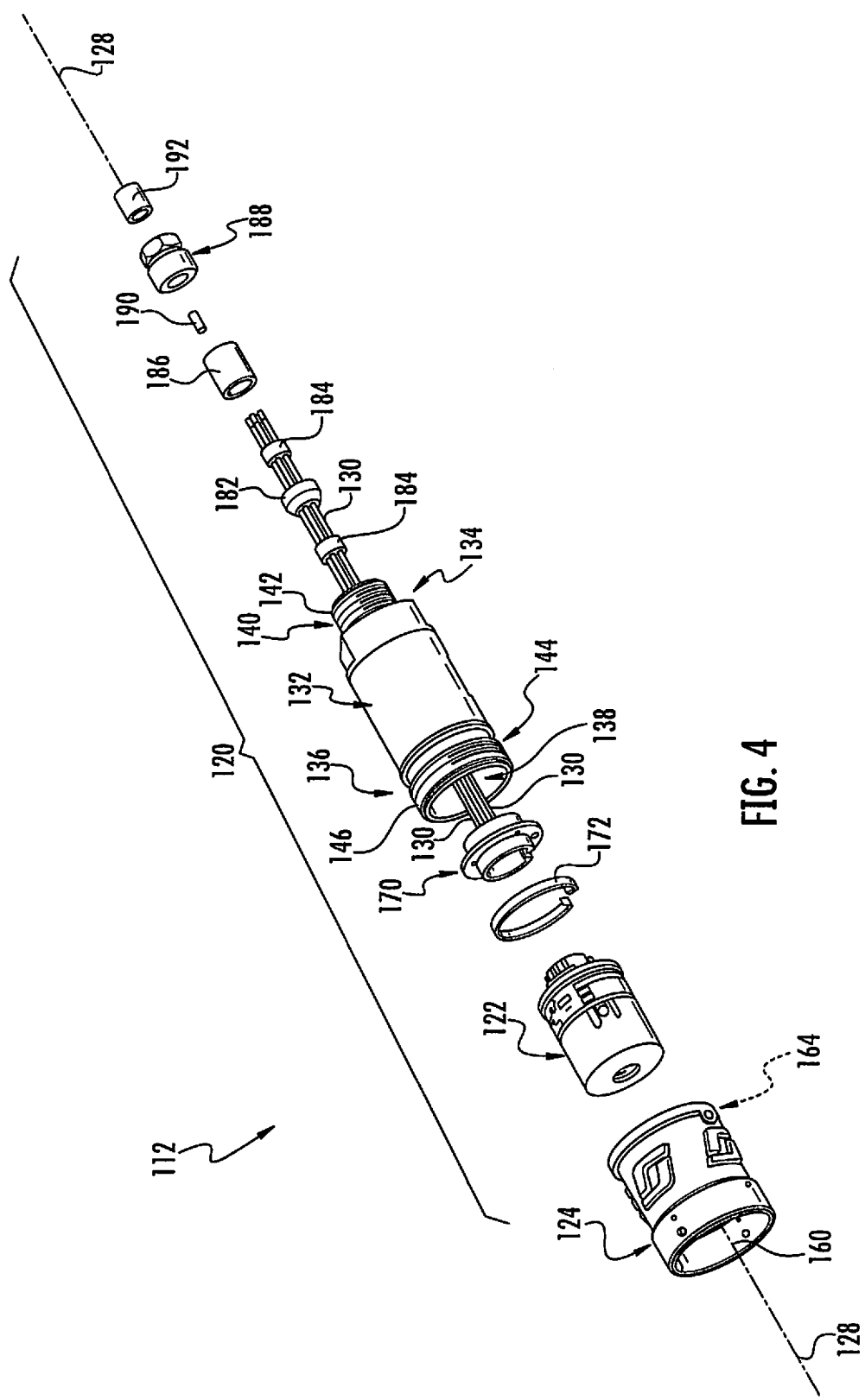
FIG. 4 is an exploded perspective view of an embodiment of a sensor of the detector assembly shown in FIG. 3.

FIG. 4 is an exploded perspective view of an embodiment of the sensor 112. The sensor 112 includes a detector head assembly 120 and a retaining cap 124. The detector head assembly 120 includes a sensor cartridge 122. The sensor 112 is elongated and extends along a central longitudinal axis 128. The detector head assembly 120 is electrically connected to the mounting structure 114 (shown in FIGS. 3 and 5), the processing component(s), the power supply component(s), and/or the communication component(s) via one or more electrical wires 130 (which may or may not be grouped together in an electrical cable).

The detector head assembly 120 includes a detector body 132. The detector body 132 extends a longitudinal length along the central longitudinal axis 128 from an end 134 to an opposite end 136. The detector body 132 includes an internal channel 138 that extends through the detector body 132 along the length of the detector body 132. The internal channel 138 extends a longitudinal length along the central longitudinal axis 128. The internal channel 138 extends into the detector body 132 through the ends 134 and 136 such that the ends 134 and 136 are open to the internal channel 138.

The detector head assembly 120 includes an attachment member 140 for mounting the sensor 112 to the mounting structure 114. In the illustrated embodiment, the attachment member 140 includes a thread 142 for threadably connecting the sensor 112 to the mounting structure 114. But, in addition or alternatively to the thread 142, the attachment member 140 may use any other mounting strategy, such as, but not limited to, an adhesive, an interference fit, a snap-fit, a latch, a clip, a clamp, a threaded fastener, and/or the like. In the illustrated embodiment, the attachment member 140 is located at the end 134 of the detector body 132, however, the attachment member 140 may have any other location along the detector body 132.

The detector head assembly 120 may include an attachment member 144 for mounting the retaining cap 124 to the detector body 132. The illustrated embodiment of the attachment member 144 includes a thread 146 that enables the retaining cap 124 to be mounted to the detector body 132 by being threadably connected to the detector body 132. In addition or alternatively to the thread 146, the attachment member 144 may use any other mounting strategy for mounting the retaining cap 124 to the detector body 132, such as, but not limited to, an adhesive, an interference fit, a snap-fit, a latch, a clip, a clamp, a threaded fastener, and/or the like. Although the attachment member 144 is shown as being formed at the end 136 of the detector body 132, the attachment member 144 may have any other location along the detector body 132.

The sensor cartridge 122 is held by the detector body 132 of the detector head assembly 120. The sensor cartridge 122 includes a sensing element (not shown) that is configured to sense one or more parameters from the environment 116 (shown in FIGS. 3 and 5). The sensing element may be any type of sensing element that is configured to sense the parameter(s) in any manner. In the illustrated embodiment, the sensing element is a diffusion type sensing element that senses the parameter(s) through diffusion. Any other type of sensing element may be used in addition or in alternative to the diffusion type sensing element described herein.

The retaining cap 124 is configured to be mounted to the detector body 132. When mounted to the detector body 132, the retaining cap 124 extends at least partially around the sensor cartridge 122 for protecting the sensor cartridge 122 from damage (e.g., impact damage). The sensing element of the sensor cartridge 122 is exposed to the environment 116 through an internal passage 160 of the retaining cap 124, which is open to the environment 116. The interior passage 160 optionally includes a screen (not shown) to facilitate preventing debris from entering the interior passage 160 and possibly fouling the sensor element.

The retaining cap 124 includes an attachment member 164 for mounting the retaining cap 124 to the detector body 132. In the illustrated embodiment, the attachment member 164 includes a thread (not shown) that enables the retaining cap 124 to be mounted to the detector body 132 by threadably connecting the retaining cap 124 to the thread 146 of the detector body 132. Additionally or alternatively, the attachment member 164 may use any other mounting strategy for mounting the retaining cap 124 to the detector body 132, such as, but not limited to, an adhesive, an interference fit, a snap-fit, a latch, a clip, a clamp, a threaded fastener, and/or the like. The attachment member 164 may have any location along the retaining cap 124.

In the illustrated embodiment, the detector head assembly 120 includes an electrical connector 170 that is held by the detector body 132 within the internal channel 138. The connector 170 is operatively (e.g., electrically and/or optically) connected to the electrical wires 130. The connector 170 is configured to mate with the sensor cartridge 122 to operatively connect the sensing element of the sensor cartridge 122 to the wires 130 and thereby to the processing component(s), the power supply component(s), and/or the communication component(s). The connector 170 may be an optical and/or an electrical connector. The connector 170 is optionally retained within the internal channel 138 of the detector body 132 with a retaining ring 172.

As will be described below, the detector head assembly 120 includes a wire seal 180 that is configured to seal the wires 130 to the detector body 132 and each other to facilitate preventing a combustion and/or an explosion that occurs within the interior chamber 118 (shown in FIGS. 3 and 5) of the mounting structure 114 from extending into the environment 116 through the internal channel 138 of the detector body 132. The wire seal 180 includes a generally pliable sealant 182. The wire seal 180 may also include a generally rigid sealant 184, a sleeve 186, a compression nut 188, an anti-rotation pin 190, and/or an elastomeric sleeve 192.

Figure 5:
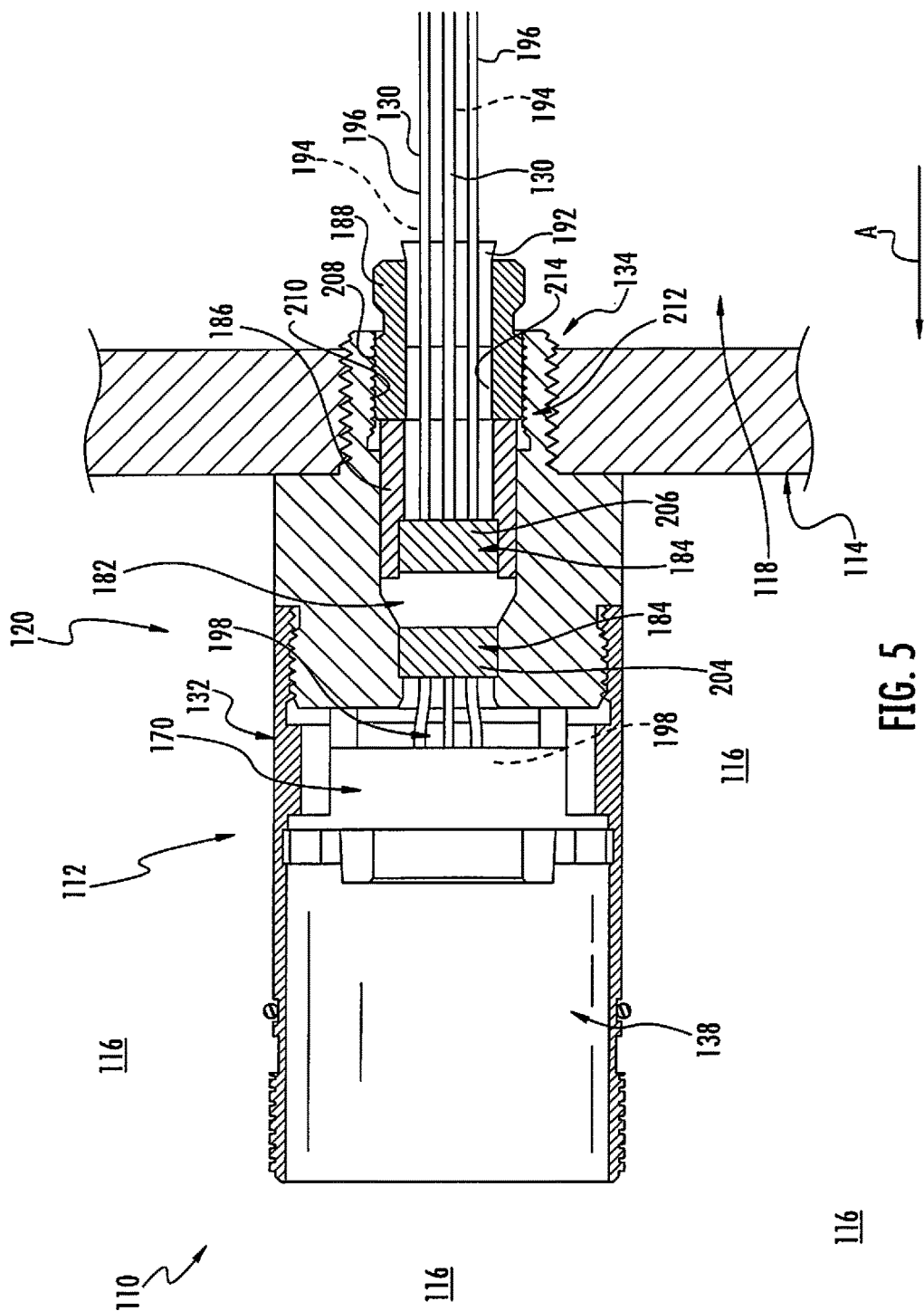
FIG. 5 is a cross-sectional view of the detector assembly shown in FIG. 3.

FIG. 5 is a cross-sectional view of the detector assembly 110. As can be seen in FIG. 5, the detector body 132 of the sensor 112 is mounted to the mounting structure 114 such that the internal channel 138 of the detector body 132 is aligned in fluid communication with the interior chamber 118 of the mounting structure 114 through the end 134.

As can be seen in FIG. 5, the sensor 112 includes a plurality of the wires 130 in the illustrated embodiment. But, the sensor 112 may include any number of the wires 130, including embodiments wherein the sensor 112 only includes one of the wires 130. Each wire 130 includes a conductor 194 and an insulation layer 196 surrounding the conductor 194. The conductor 194 of each wire 130 may be an electrical conductor or an optical conductor. In some embodiments, one or more of the wires 130 includes an electrical conductor 194 and one or more of the wires 130 includes an optical conductor 194. As can be seen in FIG. 5, each wire 130 extends from the interior chamber 118 of the mounting structure 114 and into the internal channel 138 of the detector body 132 through the end 134 such that ends 198 of the conductors 194 are operatively (e.g., electrically and/or optically) connected to the connector 170.

As briefly described above, the wire seal 180 is configured to seal the wires 130 to the detector body 132 and each other to facilitate preventing a combustion and/or an explosion that occurs within the interior chamber 118 of the mounting structure from extending into the environment 116 through the internal channel 138 of the detector body 132. The wire seal 180 includes the generally pliable sealant 182, which is configured to be longitudinally compressed along the longitudinal length of the internal channel 138 of the detector body 138 during assembly of the detector head assembly 120 such that the generally pliable sealant 182 fills one or more voids (e.g. the voids 220, 222, and 224 shown in FIG. 6) between the wires 130 and the detector body 132. The generally pliable sealant 182 is configured to flow under dynamic pressure when exposed to at least one of an explosive gas pressure or an explosive vapor pressure.

The generally pliable sealant 182 may have any level of pliability that enables the generally pliable sealant 182 to function as described and/or illustrated herein. The generally pliable sealant 182 may be fabricated from any material(s) that enables the generally pliable sealant 182 to function as described and/or illustrated herein. Non-limiting examples of materials used to fabricate the generally pliable sealant 182 include, but are not limited to, a semi-rigid and/or expanded polymer (such as, but not limited to, polytetrafluoroethylene (Teflon) and/or the like), an elastomer (such as, but not limited to natural rubber, graphite, isoprene, styrene-butadiene, butyl, ethylene propylene, nitrile, neoprene, chlorosulphonated polyethylene, silicone, fluorosilicone, and/or the like), graphite, graphite Grade GHA-J with a corrosion resistant inhibitor, and/or the like.

In the illustrated embodiment, the wire seal 180 includes the generally rigid sealant 184, which is configured to facilitate the longitudinal compression of the generally pliable sealant 184. The generally rigid sealant 184 may have any level of rigidity that enables the generally rigid sealant 184 to function as described and/or illustrated herein. The generally rigid sealant 184 may be fabricated from any material(s) that enables the generally rigid sealant 184 to function as described and/or illustrated herein. Non-limiting examples of materials used to fabricate the generally rigid sealant 184 include, but are not limited to, a polymer (such as, but not limited to, polytetrafluoroethylene (Teflon), polyphenylene sulfide, polysulfone, polyethersulfone, polyetheretherketone, polyetherimide, polyphenylene oxide), a ceramic, a metal (with and without protective coatings), ceramic $Al_2O_3$ of at least approximately 96% purity, and/or the like.

As shown in FIG. 5, the generally pliable sealant 182 is held within the internal channel 138 of the detector body 132. The wires 130 extend through preformed holes 200 (shown in FIG. 6) of the generally pliable sealant 182 such that the generally pliable sealant 182 surrounds the wires 130 and extends between the detector body 132 and the wires 130.

The generally rigid sealant 184 is held within the internal channel 138 of the detector body 132. The wires 130 extend through preformed holes 202 (shown in FIG. 6) of the generally rigid sealant 184 such that the generally rigid sealant 184 surrounds the wires 130 and extends between the detector body 132 and the wires 130. In the illustrated embodiment, the generally rigid sealant 184 includes a first rigid sealant segment 204 and a second rigid sealant segment 206 that are spaced apart along the longitudinal length of the internal channel 138. The generally pliable sealant 182 is positioned along the longitudinal length of the internal channel 138 between the first rigid sealant segment 204 and the second rigid sealant segment 206. In other words, the generally pliable sealant 182 is held within the internal channel 138 such that the generally pliable sealant 182 is sandwiched between the first rigid sealant segment 204 and the second rigid sealant segment 206 along the longitudinal length of the internal channel 138.

The sleeve 186 of the wire seal 180 is held within the internal channel 138 of the detector body 132 such that the sleeve 186 is engaged in physical contact with the generally pliable sealant 182 and/or the second generally rigid sealant segment 206. In the illustrated embodiment, the sleeve 186 is engaged in physical contact with both the generally pliable sealant 182 and the second generally rigid sealant segment 206. The sleeve 186 is held within the internal channel 138 such that the sleeve 186 extends between the second rigid sealant segment 206 and the compression nut 188 along the longitudinal length of the internal channel 138.

The compression nut 188 includes an exterior thread 208 that is threadably connected to an interior thread 210 of the end 134 of the detector body 132. As can be seen in FIG. 5, an end 212 of the compression nut 188 is engaged in physical contact with the sleeve 186. The compression nut 188 includes an opening 214 through which the wires 130 extend. The elastomeric (e.g., rubber and/or the like) sleeve 192 is optionally positioned within the opening 214 around the wires 130 to facilitate preventing damage to the insulation layers 196 of the wires 130.

As briefly described above, the generally pliable sealant 182 is configured to be longitudinally compressed along the longitudinal length of the internal channel 138 of the detector body 132 to seal the wires 130 to the detector body 132 and each other. Specifically, during assembly of the detector head assembly 120, the generally pliable sealant 182 is longitudinally compressed by threading the compression nut 188 into the end 134 of the detector body 132 in the direction of the arrow A of FIG. 5. As the compression nut 188 moves in the direction A, the compression nut 188 moves the sleeve 186 along the longitudinal length of the internal channel 138 in the direction A. The optional anti-rotation pin 190 (shown in FIG. 4) is engaged in physical contact with the sleeve 186 to facilitate preventing the sleeve from rotating along with the compression nut 188 as the compression nut 188 is threaded into the end 134 of the detector body 132. As the sleeve 186 moves along the longitudinal length of the internal channel 138 in the direction A, the engagement of the sleeve 186 with the generally pliable sealant 182 and the second rigid sealant segment 206 longitudinally compresses the generally pliable sealant 182 between the first rigid sealant segment 204 and the second rigid sealant segment 206. The generally pliable sealant 182 may be longitudinally compressed by any amount that enables the wire seal 180 to seal the wires 130 to the detector body 132 within the internal channel 138. The amount of longitudinal compression of the generally pliable sealant 182 may be controlled by controlling the amount of rotationally torque of the compression nut 188.

As the generally pliable sealant 182 is longitudinally compressed, the generally pliability of the generally pliable sealant 182 causes the generally pliable sealant 182 to flow and thereby move into and fill one or more voids 220, 222, and/or 224 (shown in FIG. 6) between the wires 130 and the detector body 132.

Figure 6:
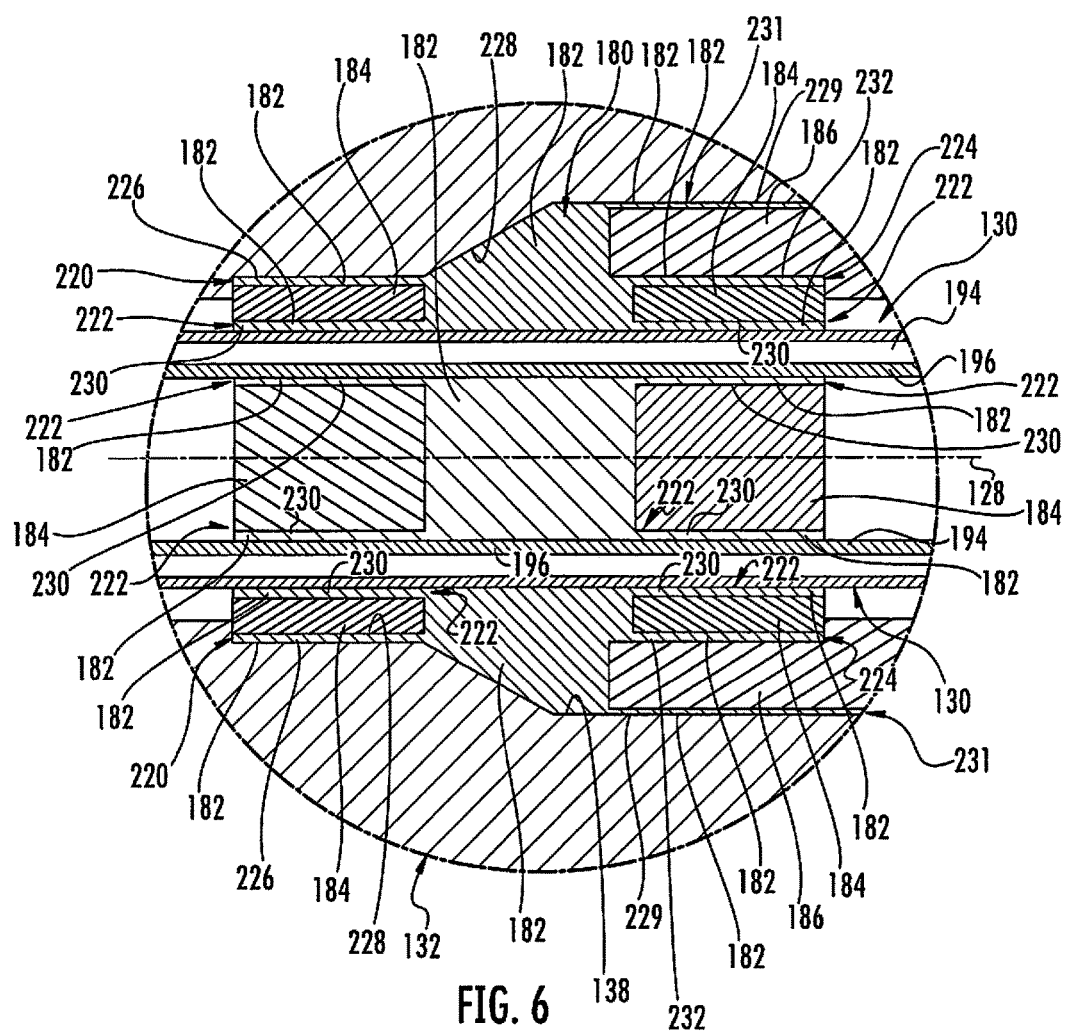
FIG. 6 is a cross-sectional view of the sensor shown in FIG. 4 illustrating an embodiment of movement of an embodiment of a generally pliable sealant of the sensor.

Specifically, and referring now to FIG. 6, the generally pliable sealant 182 has been longitudinally compressed such that the generally pliable sealant 182 has flowed and thereby moved into and filled the voids 220, 222, and 224 that between the wires 130 and the detector body 132. As can be seen in FIG. 6, segments 226 of the generally pliable sealant 182 have moved into and filled the voids 220, which extend between the generally rigid sealant 184 and an interior surface 228 of the detector body 132. Optionally, segments 229 of the generally pliable sealant 182 have moved into and filled voids 231 that extend between the sleeve 186 and the detector body 182. Segments 230 of the generally pliable sealant 182 have moved into and filled the voids 222, which extend between the generally rigid sealant 184 and the insulation layers 196 of the wires 130. Segments 232 of the generally pliable sealant 182 have moved into and filled the voids 224, which extend between the sleeve 186 and the generally rigid sealant 184.

By filling the voids 220, 222, and 224 (and optionally the voids 231, which may or may not be present), the generally pliable sealant 182 creates a seal that seals the wires 130 to the detector body 132 and to each other. The seal created by the longitudinal compression of the generally pliable sealant 182 may facilitate preventing a combustion and/or an explosion that occurs within the interior chamber 118 (shown in FIGS. 3 and 5) of the mounting structure 114 (shown in FIGS. 3 and 5) from extending into the environment 116 (shown in FIGS. 3 and 5) through the internal channel 138 of the detector body 132.

Moreover, when an explosion occurs within the interior chamber 118 of the mounting structure 114, the generally pliable sealant 182 is exposed to dynamic pressure from the explosive gas pressure and/or the explosive vapor pressure. The general pliability of the generally pliable sealant 182 enables the sealant 182 to flow under the dynamic pressure when exposed to the explosive gas pressure and/or explosive vapor pressure. The flow of the generally pliable sealant 182 under the dynamic pressure provides an increase in seal pressure between the generally pliable sealant 182 and the wires 130 and detector body 132, which may facilitate maintaining the seal between the wires 130 and the detector body 132 (and between the individual wires 130) during such an explosion within the interior chamber 118 of the mounting structure 114.

The wire seal 180 may provide a stronger seal than at least some known wire seals for detector assemblies. In some embodiments, the wire seal 180 may enable the detector assembly 110 to be used at operating temperatures from approximately −40° C. to approximately +85° C. In some embodiments, the wire seal 180 may capable of withstanding explosion pressures of up to approximately 6000 pounds per square inch (psi; approximately 413.685 Bar).

In an embodiment, the subject matter described and/or illustrated herein relates generally to a Gas Detection Head with sealed wire leads for use in potentially hazardous areas where explosive gas or vapors may be present in the atmosphere. The subject matter described and/or illustrated herein may include improvements in the method used to seal the wiring in the detector head assembly such that when the detector head is mounted in an explosion proof enclosure the wire seal will not allow explosive gas or vapor to penetrate the wire seal.

In an embodiment, the subject matter described and/or illustrated herein may provide improvements in the method of sealing the wiring from the sensor connector as it passes through the detector head housing to the electronics inside an explosion proof enclosure. The subject matter described and/or illustrated herein may eliminate the use of heat cured epoxy sealants.

In an embodiment, an explosive proof gas detection head device with dynamic flame path wire seal has an explosion proof housing and a sensor connector assembly having a plurality of sensor connection wires. The sensor connection wires have single round solid conductors therein and a two component seal system. The seal system includes a thickness of pliable sealant and a rigid sealant.

In an embodiment, an explosive proof gas detection head device with dynamic flame path wire seal includes an explosion proof housing, and a sensor connector assembly having a plurality of sensor connection wires. The sensor connection wires have single round solid conductors therein. The explosive proof gas detection head device includes a two component seal system. The seal system includes a thickness of pliable and rigid sealant. In an aspect, the pliable and rigid sealants include preformed graphite Grade GHA-J with a corrosion resistant inhibitor pliable sealant and ceramic $Al_2O_3$, at least 96% pure, respectively. In an aspect, the pliable sealant is between two rigid sealants.

As used herein, an element or step recited in the singular and proceeded with the word "a" or "an" should be understood as not excluding plural of said elements or steps, unless such exclusion is explicitly stated. Furthermore, references to "one embodiment" or "an embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A detector head assembly of a sensor, the detector head assembly comprising:
    a detector body comprising an internal channel extending a longitudinal length, the detector body being configured to hold a sensor cartridge that includes a sensing element;
    a wire comprising a conductor, the wire extending into the internal channel of the detector body such that an end of the conductor is configured to be operatively connected to the sensing element; and
    a wire seal comprising a generally pliable sealant held within the internal channel of the detector body, wherein the generally pliable sealant is configured to be longitudinally compressed along the longitudinal length of the internal channel during assembly of the detector head assembly such that the generally pliable sealant moves into and fills one or more voids between the wire and the detector body for sealing the wire to the detector body, the wire seal further comprising a generally rigid sealant held within the internal channel of the detector body, the wire extending through the generally rigid sealant such that the generally rigid sealant surrounds the wire and extends between the detector body and the wire, the one or more voids filled by the generally pliable sealant during the longitudinal compression thereof include at least one of a void that extends between the generally rigid sealant and the detector body and a void that extends between the generally rigid sealant and the wire.

2. The detector head assembly of claim 1, wherein the generally pliable sealant is configured to flow under dynamic pressure when exposed to at least one of an explosive gas pressure or an explosive vapor pressure.

3. The detector head assembly of claim 1, wherein the generally rigid sealant comprises a first rigid sealant segment and a second rigid sealant segment, the generally pliable sealant being sandwiched between the first and second rigid sealant segments along the longitudinal length of the internal channel, wherein the generally pliable sealant is configured to be longitudinally compressed between the first and second rigid sealant segments.

4. The detector head assembly of claim 1, further comprising a sleeve that extends within the internal channel of the detector body, the sleeve being configured to engage in physical contact with at least one of the generally pliable sealant or a generally rigid sealant that is held within the internal channel to longitudinally compress the generally pliable sealant during assembly of the detector head assembly.

5. The detector head assembly of claim 1, further comprising a sleeve and a compression nut, the sleeve extending within the internal channel of the detector body, the compression nut being threadably connected to the detector body and being engaged in physical contact with the sleeve, wherein the compression nut is configured to be threaded into the detector body to move the sleeve along the longitudinal length of the internal channel and thereby longitudinally compress the generally pliable sealant.

6. The detector head assembly of claim 1, wherein at least one of the generally pliable sealant or a generally rigid sealant that is held within the internal channel comprises a pre-formed hole through which the wire extends before the generally pliable sealant has been longitudinally compressed.

7. The detector head assembly of claim 1, wherein the generally pliable sealant comprises at least one of a semi-rigid polymer, an expanded polymer, an elastomer, graphite, or graphite Grade GHA-J.

8. The detector head assembly of claim 1, wherein the generally rigid sealant comprises at least one of a polymer, a ceramic, a metal, or ceramic $Al_2O_3$ of at least approximately 96% purity.

9. A detector head assembly of a sensor, the detector head assembly comprising:
    a detector body comprising an internal channel extending a longitudinal length, the detector body being configured to hold a sensor cartridge that includes a sensing element;
    a wire comprising a conductor, the wire extending into the internal channel of the detector body such that an end of the conductor is configured to be operatively connected to the sensing element;

a wire seal comprising a generally pliable sealant held within the internal channel of the detector body, wherein the generally pliable sealant is configured to be longitudinally compressed along the longitudinal length of the internal channel during assembly of the detector head assembly such that the generally pliable sealant moves into and fills one or more voids between the wire and the detector body for sealing the wire to the detector body; and a sleeve and a compression nut, the sleeve extending within the internal channel of the detector body, the compression nut being threadably connected to the detector body and being engaged in physical contact with the sleeve, the compression nut is configured to be threaded into the detector body to move the sleeve along the longitudinal length of the internal channel and thereby longitudinally compress the generally pliable sealant, the detector head assembly further comprising an anti-rotation pin that is engaged in physical contact with the sleeve for preventing the sleeve from rotating along with the compression nut.

10. A detector assembly comprising:

a mounting structure having an interior chamber; and a sensor configured to be mounted to the mounting structure, the sensor comprising:

a detector body comprising an internal channel extending a longitudinal length, the detector body being configured to hold a sensor cartridge that includes a sensing element, the detector body being configured to be mounted to the mounting structure such that the internal channel communicates with the interior chamber of the mounting structure;

a wire comprising a conductor, the wire extending from the interior chamber of the mounting structure and into the internal channel of the detector body such that an end of the conductor is configured to be operatively connected to the sensing element; and a wire seal comprising a generally pliable sealant held within the internal channel of the detector body, the generally pliable sealant is configured to be longitudinally compressed along the longitudinal length of the internal channel during assembly of the detector assembly such that the generally pliable sealant moves into and fills one or more voids between the wire and the detector body for sealing the wire to the detector body, the wire seal further comprising a generally rigid sealant held within the internal channel of the detector body, the wire extending through the generally rigid sealant such that the generally rigid sealant surrounds the wire and extends between the detector body and the wire, the one or more voids filled by the generally pliable sealant during the longitudinal compression thereof include at least one of a void that extends between the generally rigid sealant and the detector body or a void that extends between the generally rigid sealant and the wire.

11. The detector assembly of claim 10, wherein the generally pliable sealant is configured to flow under dynamic pressure when exposed to at least one of explosive gas pressure or explosive vapor pressure.

12. The detector assembly of claim 10, wherein the generally rigid sealant comprises a first rigid sealant segment and a second rigid sealant segment, the generally pliable sealant being sandwiched between the first and second rigid sealant segments along the longitudinal length of the internal channel, wherein the generally pliable sealant is configured to be longitudinally compressed between the first and second rigid sealant segments.

13. The detector assembly of claim 10, further comprising a sleeve that extends within the internal channel of the detector body, the sleeve being configured to engage in physical contact with at least one of the generally pliable sealant or a generally rigid sealant that is held within the internal channel to longitudinally compress the generally pliable sealant during assembly of the detector assembly.

14. The detector assembly of claim 10, further comprising a sleeve and a compression nut, the sleeve extending within the internal channel of the detector body, the compression nut being threadably connected to the detector body and being engaged in physical contact with the sleeve, wherein the compression nut is configured to be threaded into the detector body to move the sleeve along the longitudinal length of the internal channel and thereby longitudinally compress the generally pliable sealant.

15. The detector assembly of claim 10, wherein at least one of the generally pliable sealant or a generally rigid sealant that is held within the internal channel comprises a pre-formed hole through which the wire extends before the generally pliable sealant has been longitudinally compressed.

16. The detector assembly of claim 10, wherein the generally pliable sealant comprises at least one of a semi-rigid polymer, an expanded polymer, an elastomer, graphite, or graphite Grade GHA-J.

17. The detector assembly of claim 10, wherein the generally rigid sealant comprises at least one of a polymer, a ceramic, a metal, or ceramic $Al_2O_3$ of at least approximately 96% purity.

* * * * *